US00PP31273P2

(12) United States Plant Patent
Lübben

(10) Patent No.: US PP31,273 P2
(45) Date of Patent: Dec. 24, 2019

(54) ***GERANIUM* PLANT NAMED 'AZRU12'**

(50) Latin Name: ***Geranium wallichianum* x *Geranium himalayense***
Varietal Denomination: AZRU12

(71) Applicant: Dietmar Lübben, Edewecht (DE)

(72) Inventor: Dietmar Lübben, Edewecht (DE)

(73) Assignee: Zu Jeddeloh Pflanzenhandels GmbH, Edewecht (DE)

( * ) Notice: Subject to any disclaimer, the term of this patent is extended or adjusted under 35 U.S.C. 154(b) by 0 days.

(21) Appl. No.: 16/350,431

(22) Filed: Nov. 14, 2018

(51) Int. Cl.
*A01H 5/02* (2018.01)
*A01H 6/42* (2018.01)

(52) U.S. Cl.
USPC ..... Plt./324
CPC ..... *A01H 6/42* (2018.05)

(58) Field of Classification Search
USPC ..... Plt./324
See application file for complete search history.

(56) References Cited

PUBLICATIONS

UPOV hit on *Geranium* plant named, 'AZRU12', QZ PBR 20181334, filed May 18, 2018.*

* cited by examiner

*Primary Examiner* — Anne Marie Grunberg

(57) ABSTRACT

A new cultivar of *Geranium* plant named 'AZRU12' that is characterized by light lavender flowers with purple veins, a long flowering season, good heat tolerance and a mounding plant habit.

1 Drawing Sheet

Botanical classification: *Geranium wallichianum* x *Geranium himalayense.*

Variety denomination: 'AZRU12'.

BACKGROUND OF THE INVENTION

The present invention relates to a new and distinct cultivar of *Geranium* plant botanically known as *Geranium wallichianum* x *Geranium himalayense* and hereinafter referred to by the cultivar name 'AZRU12'.

'AZRU12' was discovered in 2012 as a naturally occurring whole plant mutation of *Geranium* 'Azure Rush' (U.S. Plant Pat. No. 22,684). The new *Geranium* was discovered and selected by the Inventor as a single flowering plant from within a population of plants of 'Azure Rush' in a controlled greenhouse environment in a cultivated area of Edewecht, Germany.

Asexual propagation of the new cultivar 'AZRU12' first occurred by division in 2012 in Edewecht, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Geranium* cultivar 'AZRU12'. These traits in combination distinguish 'AZRU12' as a new and distinct cultivar apart from other existing known varieties of *Geranium.*

1. *Geranium* 'AZRU12' exhibits light lavender flowers with purple veins.
2. *Geranium* 'AZRU12' exhibits a long flowering season.

3. *Geranium* 'AZRU12' exhibits good heat tolerance.
4. *Geranium* 'AZRU12' exhibits a mounding plant habit.

The closest comparison cultivars are *Geranium* 'Boo' (U.S. Plant Pat. No. 27,885) and *Geranium* 'Rozanne' (U.S. Plant Pat. No. 12,175). 'AZRU12' is distinguishable from 'Boo' by the following characteristics:

1. 'AZRU12' exhibits light lavender flowers with purple veins. In contrast, 'Boo' has mauve-pink flowers with whitish centers and dark violet veins.
2. *Geranium* 'AZRU12' exhibits flower petals that slightly overlap. In contrast, the flower petals of 'Boo' do not overlap.
3. *Geranium* 'AZRU12' exhibits good heat tolerance. In contrast, 'Boo' has poorer heat tolerance.
4. *Geranium* 'AZRU12' exhibits a mounding plant habit. In contrast, 'Boo' has a flatter more spreading plant habit.

'AZRU12' is distinguishable from 'Rozanne' by the following characteristics:

1. 'AZRU12' exhibits light lavender flowers with purple veins. In contrast, 'Rozanne' has blue flowers with whitish centers and dark purple veins.

'AZRU12' is distinguishable from the parent plant 'Azure Rush' by the following characteristics:

1. 'AZRU12' exhibits light lavender flowers with purple veins. In contrast, 'Azure Rush' has mauve-blue flowers with dark purple veins.

BRIEF DESCRIPTION OF THE DRAWING

The accompanying photograph illustrates the distinguishing traits of *Geranium* 'AZRU12'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Geranium* cultivar named 'AZRU12'. Data was collected in Heidesheim, Germany from 12 month old outdoor grown plants in 25 cm. diameter containers. The time of year was Summer and the temperature range was 15-28 degrees Centigrade during the day and 8-15 degrees Centigrade at night. No growth retardants were used. Color determinations are in accordance with The Royal Horticultural Society Colour Chart 2007 edition, except where general color terms of ordinary dictionary significance are used. The growing requirements are similar to the species. 'AZRU12' has not been tested under all possible conditions and phenotypic differences may be observed with variations in environmental, climatic, and cultural conditions, however, without any variance in genotype.

Botanical classification: *Geranium wallichianum* x *Geranium himalayense* 'AZRU12'.

Annual or perennial: Perennial.

Parentage: 'AZRU12' is a naturally occurring whole plant mutation of *Geranium* 'Azure Rush'.

Vigor: Strong.

Growth habit: Spreading.

Plant shape: Mounding.

Suitable container size: 20 cm.

Overall plant dimensions: Average 37 cm. in height and 58 cm. in diameter.

Low temperature tolerance: −20° Centigrade.

High temperature tolerance: 40° Centigrade.

Propagation: Division and tissue culture.

Time to initiate roots in summer: 15 days to initiate roots at 22° Centigrade.

Time to initiate roots in winter: 18 days to initiate roots at 20° Centigrade.

Time to produce a rooted cutting or liner in summer: 40 days at 22° Centigrade.

Time to produce a rooted cutting or liner in winter: 45 days at 20° Centigrade.

Crop time: Approximately 22 weeks.

Root system: Fine and fibrous.

Stem:

- *Branching habit.*—Freely branching.
- *Basal branching.*—Yes.
- *Average number of lateral branches.*—19.
- *Pinching.*—No.
- *Lateral branch dimensions.*—3.0 mm. in diameter and 75 cm. in length.
- *Internode length.*—11.0 cm.
- *Stem texture.*—Smooth.
- *Stem strength.*—Moderate.
- *Stem color.*—145A.
- *Pubescence.*—Pilose.

Foliage:

- *Leaf arrangement.*—Opposite.
- *Compound or single.*—Single.
- *Number of leaves per lateral branch.*—Average 10.
- *Leaf shape.*—Palmately divided, lobed and toothed.
- *Leaf apex.*—Acute.
- *Leaf base.*—Sagittate.
- *Leaf dimensions.*—Average 4.5 cm. in length and 8.0 cm. in width.
- *Texture.*—Short hairs on both surfaces.
- *Leaf margin.*—Dentate.
- *Venation pattern.*—Palmate.
- *Young leaf color (upper surface).*—143C to 144A.
- *Young leaf color (lower surface).*—145B.
- *Mature leaf color (upper surface).*—143A to 146A.
- *Mature leaf color (lower surface).*—138B.
- *Vein color (upper surface).*—146C.
- *Vein color (lower surface).*—146C.
- *Petiole dimensions.*—11.0 cm. in length and 1.5 mm. in diameter.
- *Petiole color.*—146C.
- *Durability of foliage to stress.*—Moderate.

Flower:

- *Inflorescence arrangement.*—Axillary racemes with rotate flowers.
- *Inflorescence dimensions.*—4.0 cm. in height and 9.0 cm. in width.
- *Quantity of flowers per inflorescence.*—2.
- *Quantity of flowers per lateral stem.*—4.
- *Quantity of flower buds per lateral stem.*—Average 32.
- *Quantity of flowers and buds per plant.*—Average 100.
- *Natural flowering season.*—July to October.
- *Rate of flower opening.*—Every 2 to 3 days.
- *Fragrance.*—None.
- *Flower bud length.*—12 mm.
- *Flower bud diameter.*—8 mm. in diameter.
- *Flower bud shape.*—Ovoid.
- *Bud color.*—146B.
- *Rate of bud opening.*—2 to 3 days.
- *Flower aspect.*—Outward/upright.
- *Flower shape.*—Rotate.
- *Flower dimensions.*—4.5 cm. in diameter and 1.2 cm. in height.
- *Flower longevity.*—3 to 4 days.
- *Number of petals.*—5.
- *Fused or unfused.*—Unfused.
- *Petal arrangement.*—Rotate.
- *Petal shape.*—Obcordate.
- *Petal texture.*—Smooth on both surfaces.
- *Petal margin.*—Entire.
- *Petal apex.*—Obtuse.
- *Petal base.*—Attenuate.
- *Petal dimensions.*—2.5 cm. in length and 2.0 cm in width.
- *Petal color when opening (upper side).*—91A to 91B, veins N80A.
- *Petal color when opening (under side).*—91A to 91B, veins N80A.
- *Petal color fully opened (upper side).*—91A to 91B, veins N80A.
- *Petal color fully opened (under side).*—91A to 91B, veins N80A.
- *Self-cleaning or persistent.*—Self-cleaning.

Calyx:

- *Calyx dimensions.*—1.3 cm. in length and 4.0 cm. in diameter.

Sepals:

- *Sepal arrangement.*—Rotate.
- *Number of sepals.*—5.
- *Sepal shape.*—Ovate.
- *Sepal margin.*—Entire.
- *Sepal apex.*—Acute.

*Sepal base*.—Attenuate.
*Sepal dimensions*.—1.4 cm. in length and 0.6 cm. in width.
*Young sepal color* (*upper side*).—144A.
*Young sepal color* (*under side*).—144A.
*Mature sepal color* (*upper side*).—144A.
*Mature sepal color* (*under side*).—144A.

Peduncle:
*Peduncle dimensions*.—5.0 cm. in length and 1 mm. in diameter.
*Pedicel angle*.—Upright to 40 degrees from stem.
*Peduncle strength*.—Weak.
*Peduncle color*.—144B, side facing towards sun 184A.

Pedicels:
*Pedicel dimensions*.—Average 3.7 cm. in length and 1.0 mm. in diameter.
*Pedicel strength*.—Weak.
*Pedicel color*.—146B.

Reproduction organs:
*Stamen number*.—10.
*Anther shape*.—Oblong.
*Anther size*.—2.0 mm. in length.
*Anther color*.—N79A.
*Amount of pollen*.—Low.
*Pollen color*.—154C.
*Pistil number*.—5.
*Pistil length*.—1.5 mm.
*Stigma shape*.—Linear.
*Stigma color*.—72A.
*Style length*.—3.5 mm.
*Style color*.—Near ovary 142D, center 69D, towards stigma 72A.
*Ovary color*.—144A.

Fruit and seed: Fruit and seed production have not been observed.

Disease and pest resistance: Disease and pest resistance have not been observed.

The invention claimed is:

1. A new and distinct variety of *Geranium* plant named 'AZRU12' as described and illustrated.

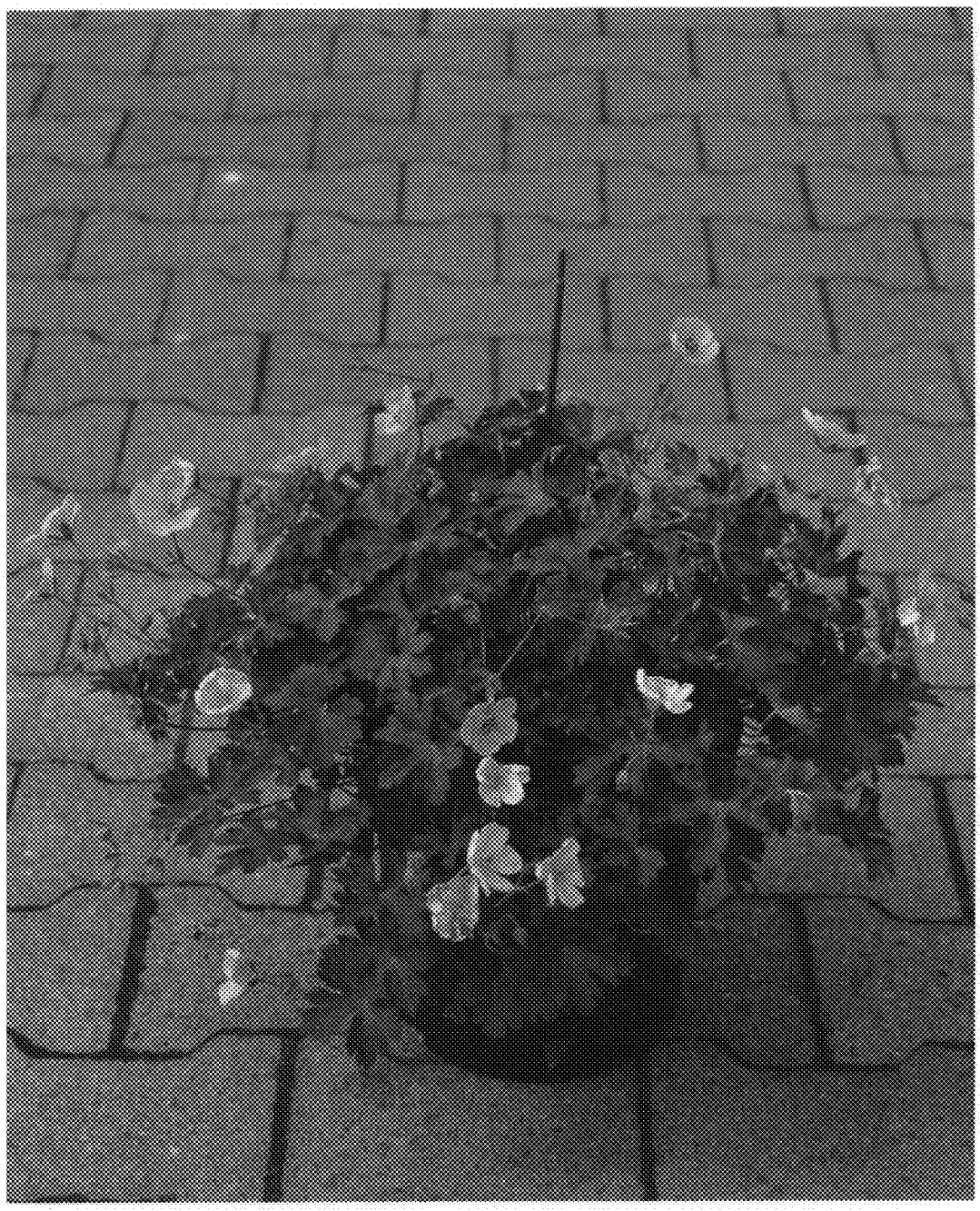

* * * * *